US010195426B2

(12) United States Patent
Kent et al.

(10) Patent No.: US 10,195,426 B2
(45) Date of Patent: Feb. 5, 2019

(54) METHOD AND APPARATUS FOR TREATING SLEEP APNEA

(71) Applicant: Invicta Medical, Inc., Santa Clara, CA (US)

(72) Inventors: Steven Thomas Kent, Portola Valley, CA (US); Laurence Wylie Harter, San Jose, CA (US); Harold Byron Kent, Portola Valley, CA (US); Karena Yadira Puldon, Northridge, CA (US)

(73) Assignee: INVICTA MEDICAL, INC., Santa Clara, CA (US)

( * ) Notice: Subject to any disclaimer, the term of this patent is extended or adjusted under 35 U.S.C. 154(b) by 54 days.

(21) Appl. No.: 14/149,689

(22) Filed: Jan. 7, 2014

(65) Prior Publication Data

US 2015/0190630 A1 Jul. 9, 2015

(51) Int. Cl.
*A61N 1/36* (2006.01)
*A61F 5/56* (2006.01)
*A61B 5/0488* (2006.01)
*A61N 1/05* (2006.01)

(52) U.S. Cl.
CPC .......... *A61N 1/3601* (2013.01); *A61B 5/0488* (2013.01); *A61F 5/56* (2013.01); *A61F 5/566* (2013.01); *A61N 1/0548* (2013.01); *A61N 1/36078* (2013.01)

(58) Field of Classification Search
CPC ............... A61N 1/0548; A61N 1/3601; A61N 1/36014; A61F 5/566; A61F 5/56–5/58; A61C 7/08; A61C 19/063–19/066; A61C 9/00–9/0013; A61M 16/0488–16/0497; A63B 71/08–71/10

USPC ............... 128/848; 607/42, 134, 48
See application file for complete search history.

(56) References Cited

U.S. PATENT DOCUMENTS

| 4,830,008 A | 5/1989 | Meer |
| 4,947,844 A * | 8/1990 | McDermott ............. A61B 5/12 607/57 |
| 5,190,053 A | 3/1993 | Meer |
| 5,284,161 A | 2/1994 | Karell |

(Continued)

FOREIGN PATENT DOCUMENTS

| CA | 2 477 540 A1 | 5/2000 |
| CN | 201361029 | 12/2009 |

(Continued)

OTHER PUBLICATIONS

Atkinson, Martin E., Anatomy for Dental Students, Mar. 14, 2013, OUP Oxford, Fourth Edition, p. 298.*

(Continued)

*Primary Examiner* — Victoria J Hicks
*Assistant Examiner* — Michelle J Lee
(74) *Attorney, Agent, or Firm* — Paradice and Li LLP

(57) ABSTRACT

An oral appliance provides electrical stimulation to a patient's tongue in a manner that prevents collapse of the tongue and/or soft palate during sleep. More specifically, the appliance may induce a reversible current or currents in a lateral direction across the tongue in a manner that shortens the patient's Palatoglossus muscle, which in turn pulls the patient's soft palate downward towards a base of the tongue, and/or decreases a volume of the tongue.

35 Claims, 14 Drawing Sheets

(56) References Cited

U.S. PATENT DOCUMENTS

| | | | |
|---|---|---|---|
| 5,792,067 A * | 8/1998 | Karell | A61N 1/0548 128/848 |
| 6,212,435 B1 * | 4/2001 | Lattner | A61N 1/3601 607/134 |
| 6,618,627 B2 | 9/2003 | Lattner et al. | |
| 6,636,767 B1 * | 10/2003 | Knudson | A61N 1/3601 128/848 |
| 7,711,438 B2 | 5/2010 | Lattner et al. | |
| 8,249,723 B2 | 8/2012 | McCreery | |
| 8,359,108 B2 | 1/2013 | McCreery | |
| 2004/0073272 A1 | 4/2004 | Knudson et al. | |
| 2007/0173893 A1 * | 7/2007 | Pitts | A61N 1/3601 607/2 |
| 2010/0185254 A1 | 7/2010 | Lindquist et al. | |
| 2011/0093036 A1 | 4/2011 | Mashiach | |
| 2011/0152965 A1 | 6/2011 | Mashiach et al. | |
| 2011/0172733 A1 | 7/2011 | Lima et al. | |
| 2011/0213438 A1 | 9/2011 | Lima et al. | |
| 2012/0192874 A1 | 8/2012 | Bolea et al. | |
| 2012/0197340 A1 | 8/2012 | Tesfayesus et al. | |
| 2012/0234331 A1 | 9/2012 | Shantha | |
| 2013/0072999 A1 | 3/2013 | Mashiach | |
| 2013/0085537 A1 | 4/2013 | Mashiach | |
| 2013/0085544 A1 | 4/2013 | Mashiach | |
| 2013/0085545 A1 | 4/2013 | Mashiach | |
| 2013/0085558 A1 | 4/2013 | Mashiach | |
| 2013/0085559 A1 | 4/2013 | Mashiach | |
| 2013/0085560 A1 | 4/2013 | Mashiach | |
| 2014/0046221 A1 | 2/2014 | Mashiach et al. | |
| 2014/0135868 A1 * | 5/2014 | Bashyam | A61F 5/566 607/42 |
| 2014/0228905 A1 * | 8/2014 | Bolea | A61N 1/0556 607/42 |
| 2015/0057719 A1 * | 2/2015 | Tang | A61N 1/0548 607/59 |
| 2015/0190630 A1 | 7/2015 | Kent et al. | |
| 2015/0224307 A1 | 8/2015 | Bolea | |

FOREIGN PATENT DOCUMENTS

| | | |
|---|---|---|
| EP | 1 128 868 B1 | 3/2010 |
| JP | 2014-158607 A | 9/2014 |
| WO | WO 2013/172935 A2 | 11/2013 |

OTHER PUBLICATIONS

Weaker, Frank, Structures of the Head and Neck, Sep. 24, 2013, F.A. Davis, p. 77.*

International Search Report and Written Opinion dated May 6, 2015, PCT Application No. PCT/US2015/010367, filed Jan. 6, 2015, 11 pages.

Invitation to Pay Additional Fees and, where Applicable, Protest Fees dated Mar. 15, 2017, PCT Application No. PCT/US2016/068599, filed Dec. 23, 2016, 2 pages.

International Search Report and Written Opinion dated May 23, 2017, PCT Application No. PCT/US2016/068599, filed Dec. 23, 2016, 21 pages.

Supplementary European Search Report dated Sep. 4, 2017, European Patent Application No. 15734842.6, filed Jan. 6, 2015, 7 pages.

* cited by examiner

METHOD AND APPARATUS FOR TREATING SLEEP APNEA

TECHNICAL FIELD

The present embodiments relate generally to sleep apnea, and specifically to non-invasive techniques for treating one or more underlying causes of sleep apnea.

BACKGROUND OF RELATED ART

Obstructive sleep apnea (OSA) is a medical condition in which a patient's upper airway is repeatedly occluded during sleep. These repeated occlusions of the upper airway may cause sleep fragmentation, which in turn may result in sleep deprivation, daytime tiredness, and malaise. More serious instances of OSA may increase the patient's risk for stroke, cardiac arrhythmias, high blood pressure, and/or other disorders.

OSA may be characterized by the tendency of the soft tissues of the upper airway to collapse during sleep, thereby occluding the upper airway. More specifically, OSA is typically caused by the collapse of the patient's soft palate and/or by the collapse of the patient's tongue (e.g., onto the back of the pharynx), which in turn may obstruct normal breathing.

There are many treatments available for OSA including, for example, surgery, constant positive airway pressure (CPAP) machines, and the electrical stimulation of muscles associated with moving the tongue. Surgical techniques include tracheotomies, procedures to remove portions of a patient's tongue and/or soft palate, and other procedures that seek to prevent collapse of the tongue into the back of the pharynx. These surgical techniques are very invasive. CPAP machines seek to maintain upper airway patency by applying positive air pressure at the patient's nose and mouth. However, these machines are uncomfortable and may have low compliance rates.

Some electrical stimulation techniques seek to prevent collapse of the tongue into the back of the pharynx by causing the tongue to protrude forward (e.g., in an anterior direction) during sleep. For one example, U.S. Pat. No. 4,830,008 to Meer discloses an invasive technique in which electrodes are implanted into a patient at locations on or near nerves that stimulate the Genioglossus muscle to move the tongue forward (e.g., away from the back of the pharynx). For another example, U.S. Pat. No. 7,711,438 to Lattner discloses a non-invasive technique in which electrodes, mounted on an intraoral device, electrically stimulate the Genioglossus muscle to cause the tongue to move forward during respiratory inspiration. In addition, U.S. Pat. No. 8,359,108 to McCreery teaches an intraoral device that applies electrical stimulation to the Hypoglossal nerve to contract the Genioglossus muscle, which as mentioned above may prevent tongue collapse by moving the tongue forward during sleep.

Moving a patient's tongue forward during sleep may cause the patient to wake, which is not desirable. In addition, existing techniques for electrically stimulating the Hypoglossal nerve and/or the Genioglossus muscle may cause discomfort and/or pain, which is not desirable. Further, invasive techniques for electrically stimulating the Hypoglossal nerve and/or the Genioglossus muscle undesirably require surgery and introduce foreign matter into the patient's tissue, which is undesirable.

Thus, there is a need for a non-invasive treatment for OSA that does not disturb or wake-up the patient during use.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

A method and apparatus for reducing the occurrence and/or severity of a breathing disorder, such as OSA, are disclosed herein. In accordance with the present embodiments, a non-invasive and removable oral appliance is disclosed that may provide electrical stimulation to a lateral and/or sublingual portion of a patient's oral cavity (mouth) in a manner that prevents a collapse of the patient's tongue and/or soft palate during sleep without disturbing (e.g., without waking) the patient. For at least some embodiments, an electric current induced by the appliance may stimulate the patient's Palatoglossus muscle in a manner that causes the Palatoglossus muscle to stiffen and shorten, which in turn may pull the patient's soft palate and/or palatal arches in a downward direction towards a base of the patient's tongue so as to prevent the soft palate from collapsing and/or from flapping against the back of the patient's throat. Stiffening and/or shortening the Palatoglossus muscle may also cause the patient's tongue to contract and/or stiffen in a manner that prevents collapse of the tongue in a posterior direction (e.g., towards the patient's pharynx). In addition, stimulating the Palatoglossus muscle using techniques described herein may also lower a superior surface of the tongue T, thereby causing the tongue to cinch downward (e.g., to "hunker down") in a manner that further prevents obstruction of the patient's upper airway. By simultaneously preventing collapse of the patient's soft palate and tongue, patency of the patient's upper airway may be maintained in a non-invasive manner. For some embodiments, the appliance may stimulate the patient's Palatoglossus muscle without moving the patient's tongue in an anterior direction. For at least one embodiment, stimulation of the patient's Palatoglossus muscle may also elevate a posterior portion of the patient's tongue, which in turn may further prevent collapse of the tongue onto the back of the patient's pharynx.

BRIEF DESCRIPTION OF THE DRAWINGS

The present embodiments are illustrated by way of example and are not intended to be limited by the figures of the accompanying drawings, where like reference numerals refer to corresponding parts throughout the drawing figures.

DETAILED DESCRIPTION

Figure 1A:
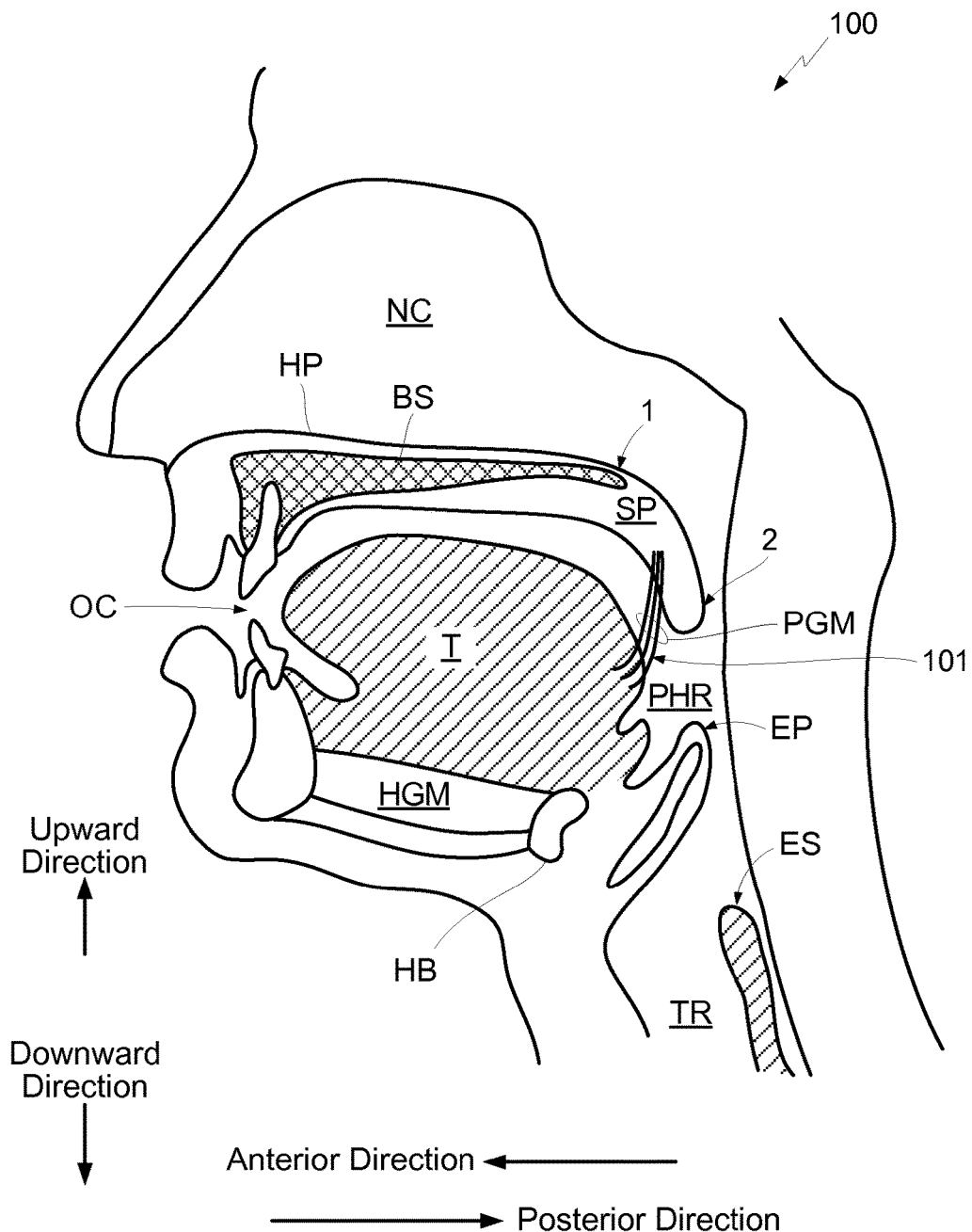
FIG. 1A is a side sectional view depicting a patient's upper airway.

A non-invasive method and apparatus for treating sleep disorders, such as obstructive sleep apnea (OSA) and/or snoring, are disclosed herein. In the following description, numerous specific details are set forth to provide a thorough understanding of the present disclosure. Also, in the following description and for purposes of explanation, specific nomenclature is set forth to provide a thorough understanding of the present embodiments. However, it will be apparent to one skilled in the art that these specific details may not be required to practice the present embodiments. In other instances, well-known circuits and devices are shown in block diagram form to avoid obscuring the present disclosure. The term "coupled" as used herein means connected directly to or connected through one or more intervening components, circuits, or physiological matter. Any of the signals provided over various buses described herein may be time-multiplexed with other signals and provided over one or more common buses. Additionally, the interconnection between circuit elements or software blocks may be shown as buses or as single signal lines. Each of the buses may alternatively be a single signal line, and each of the single signal lines may alternatively be buses, and a single line or bus might represent any one or more of a myriad of physical or logical mechanisms for communication between components. Further, the logic levels and timing assigned to various signals in the description below are arbitrary and/or approximate, and therefore may be modified (e.g., polarity reversed, timing modified, etc) as desired.

As used herein, the term "substantially lateral direction" refers to a direction across the patient's oral cavity in which the direction's lateral components are larger than the direction's anterior-to-posterior components (e.g., a substantially lateral direction may refer to any direction that is less than approximately 45 degrees from the lateral direction, as defined below with respect to the drawing figures). Further, as used herein, the term "reversible current" means a current that changes or reverses polarity from time to time between two controllable voltage potentials.

Figure 1B:
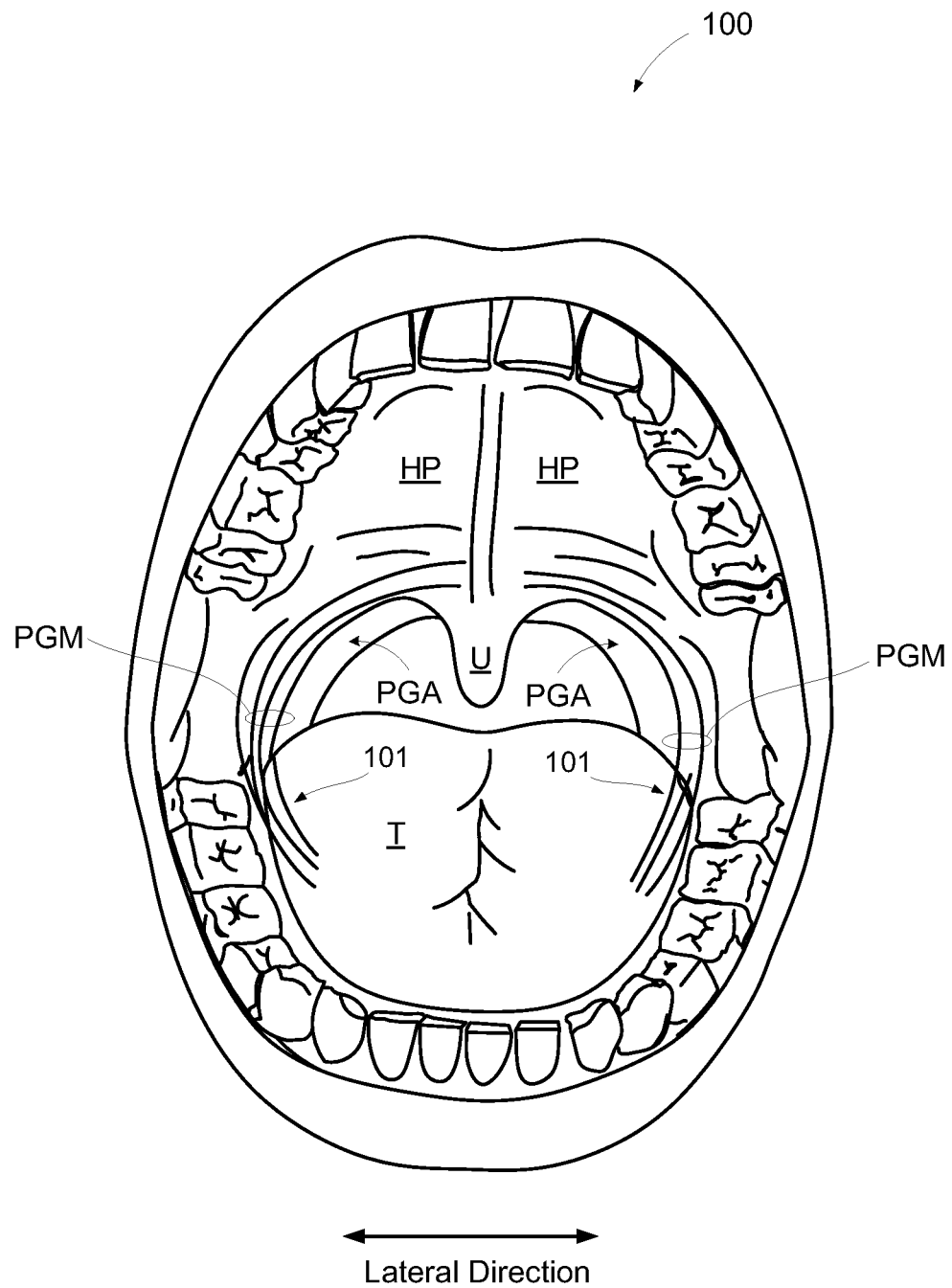
FIG. 1B is a front plan view of the patient's oral cavity.

To more fully understand the present embodiments, the dynamics of OSA are first described with respect to FIGS. 1A-1D, which illustrate the anatomical elements of a patient's upper airway 100 (e.g., including the nasal cavity, oral cavity, and pharynx of the patient). Referring first to FIGS. 1A-1B, the hard palate HP overlies the tongue T and forms the roof of the oral cavity OC (e.g., the mouth). The hard palate HP includes bone support BS, and thus does not typically deform during breathing. The soft palate SP, which is made of soft material such as membranes, fibrous material, fatty tissue, and muscle tissue, extends rearward (e.g., in a posterior direction) from the hard palate HP towards the back of the pharynx PHR. More specifically, an anterior end 1 of the soft palate SP is anchored to a posterior end of the hard palate HP, and a posterior end 2 of the soft palate SP is un-attached. Because the soft palate SP does not contain bone or hard cartilage, the soft palate SP is flexible and may collapse onto the back of the pharynx PHR and/or flap back and forth (e.g., especially during sleep).

The pharynx PHR, which passes air from the oral cavity OC and nasal cavity NC into the trachea TR, is the part of the throat situated inferior to (below) the nasal cavity NC, posterior to (behind) the oral cavity OC, and superior to (above) the esophagus ES. The pharynx PHR is separated from the oral cavity OC by the Palatoglossal arch PGA, which runs downward on either side to the base of the tongue T.

Although not shown for simplicity, the pharynx PHR includes the nasopharynx, the oropharynx, and the laryngopharynx. The nasopharynx lies between an upper surface of the soft palate SP and the wall of the throat (i.e., superior to the oral cavity OC). The oropharynx lies behind the oral cavity OC, and extends from the uvula U to the level of the hyoid bone HB. The oropharynx opens anteriorly into the oral cavity OC. The lateral wall of the oropharynx consists of the palatine tonsil, and lies between the Palatoglossal arch PGA and the Palatopharyngeal arch. The anterior wall of the oropharynx consists of the base of the tongue T and the epiglottic vallecula. The superior wall of the oropharynx consists of the inferior surface of the soft palate SP and the uvula U. Because both food and air pass through the pharynx PHR, a flap of connective tissue called the epiglottis EP closes over the glottis (not shown for simplicity) when food is swallowed to prevent aspiration. The laryngopharynx is the part of the throat that connects to the esophagus ES, and lies inferior to the epiglottis EP.

Figure 1C:
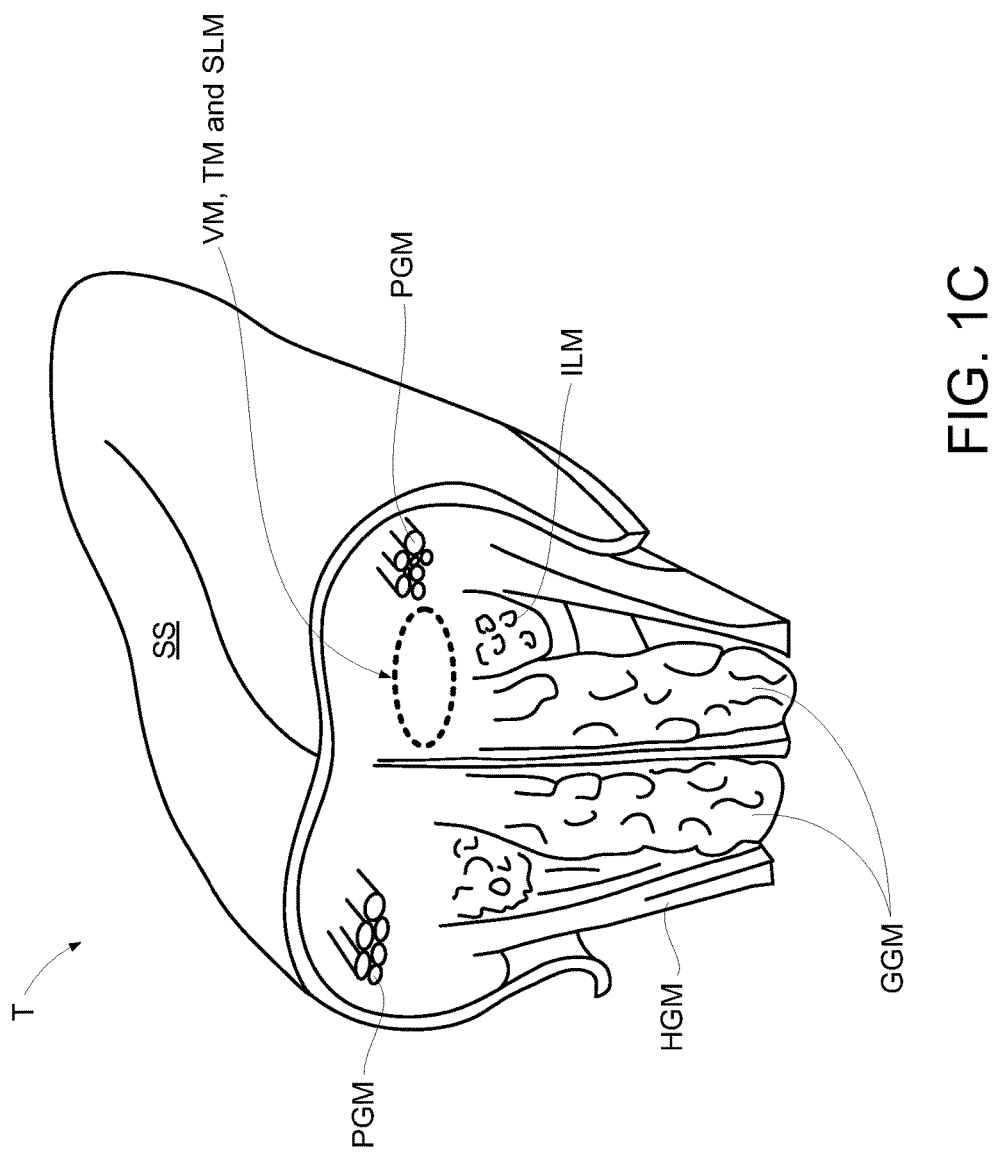
FIG. 1C is an elevated sectional view of the patient's tongue.
Figure 1D:
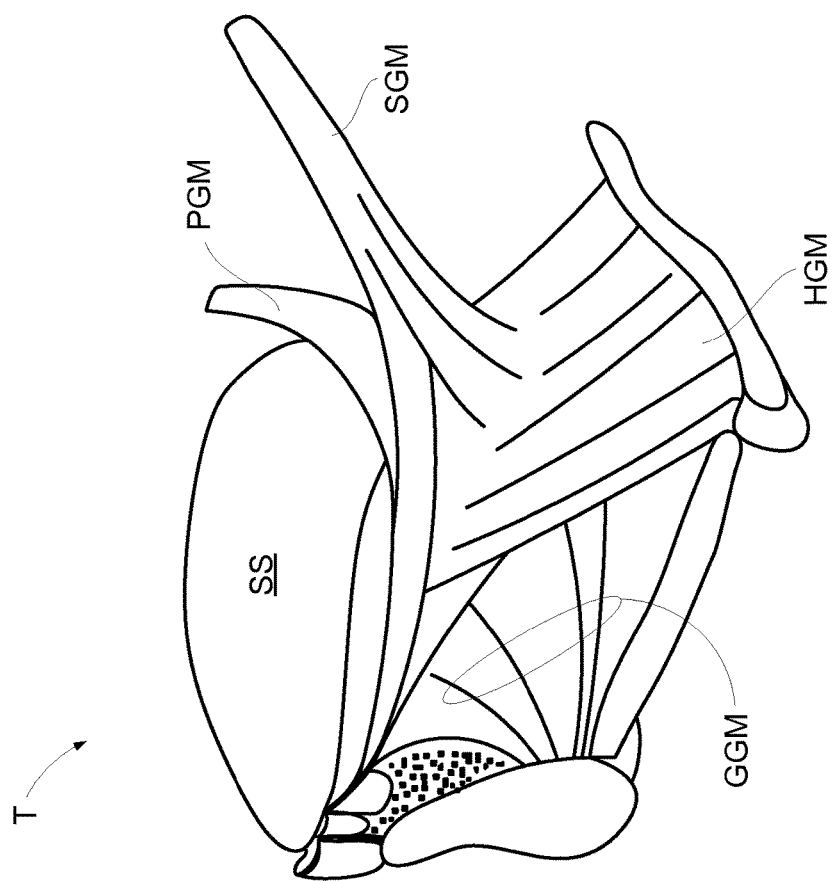
FIG. 1D is a side sectional view of the patient's tongue.

Referring also to FIGS. 1C-1D, the tongue T includes a plurality of muscles that may be classified as either intrinsic muscles or extrinsic muscles. The intrinsic muscles, which lie entirely within the tongue T and are responsible for altering the shape of the tongue T (e.g., for talking and swallowing), include the superior longitudinal muscle SLM, the inferior longitudinal muscle ILM, the vertical muscle VM, and the transverse muscle TM. The superior longitudinal muscle SLM runs along the superior surface SS of the tongue T under the mucous membrane, and may be used to elevate, retract, and deviate the tip of the tongue T. The inferior longitudinal muscle ILM lines the sides of the tongue T, and is attached to the Styloglossus muscle SGM. The vertical muscle VM is located along the midline of the tongue T, and connects the superior and inferior longitudinal muscles together. The transverse muscle TM divides the tongue at the middle, and is attached to the mucous membranes that run along the sides of the tongue T.

The extrinsic muscles, which attach the tongue T to other structures and are responsible for re-positioning (e.g., moving) the tongue, include the Genioglossus muscle GGM, the Hyoglossus muscle HGM, the Styloglossus muscle SGM, and the Palatoglossus muscle PGM. The Genioglossus muscle GGM may be used to protrude the tongue T and to depress the center of the tongue T. The Hyoglossus muscle HGM may be used to depress the tongue T. The Styloglossus muscle SGM may be used to elevate and retract the tongue T. The Palatoglossus muscle PGM may be used to depress the soft palate SP and/or to elevate the back (posterior portion) of the tongue T. Referring also to FIGS. 1A and 1B, the Palatoglossus muscle PGM connects the tongue T to both sides of the Palatoglossus arch PGA, and inserts into lateral posterior regions 101 of the base of the tongue T.

It is noted that all of the muscles of the tongue T, except for the Palatoglossus muscle PGM, are innervated by the Hypoglossal nerve (not shown for simplicity); the Palatoglossus muscle PGM is innervated by the pharyngeal branch of the vagus nerve (not shown for simplicity).

During awake periods, the muscles of the upper airway (as well as the hypoglossal nerve) are active and stimulated, and may maintain upper airway patency by preventing the soft palate SP from collapsing and/or by preventing the tongue T from prolapsing onto the back of the pharynx PHR. However, during sleep periods, a relative relaxed state of the soft palate SP may allow the soft palate SP to collapse and obstruct normal breathing, while a relative relaxed state of the tongue T may allow the tongue T to move in a posterior direction (e.g., onto the back of the pharynx PHR) and obstruct normal breathing.

Accordingly, conventional electrostimulation treatments for OSA typically involve causing the tongue T to move forward in the anterior direction during apnea episodes so that the tongue T does not collapse in the posterior direction. More specifically, some conventional techniques (e.g., disclosed in U.S. Pat. Nos. 5,190,053 and 6,212,435) electrically stimulate the Genioglossus muscle to move the tongue forward in an anterior direction during apnea episodes, while other conventional techniques (e.g., disclosed in U.S. Pat. No. 8,359,108) electrically stimulate the Hypoglossal nerve, which in turn causes the tongue to move forward in the anterior direction by innervating the Genioglossus muscle.

Unfortunately, repeatedly moving the tongue T forward (e.g., in the anterior direction) to prevent its prolapse into the back of the pharynx PHR may undesirably wake-up the patient, which defeats the very purpose of OSA treatments and may also abrade the tongue on the teeth. Indeed, electrically stimulating the relatively large Genioglossus muscle may cause discomfort or pain. In addition, because the Hypoglossal nerve innervates every tongue muscle except the Palatoglossus muscle PGM, electrically stimulating the Hypoglossal nerve may stimulate not only the Genioglossus muscle GGM but also the superior longitudinal muscle SLM, the inferior longitudinal muscle ILM, the vertical muscle VM, the transverse muscle TM, the Hyoglossus muscle HPM, and/or the Styloglossus muscle SSM. Stimulating multiple tongue muscles at the same time, in an attempt to move the tongue forward during apnea episodes, may not only over-stimulate the patient's tongue muscles but may also cause the tongue T to behave erratically (e.g., repeatedly protruding and retracting). For example, simultaneously stimulating the Genioglossus muscle GGM and the Styloglossus muscle SGM may cause the tongue T to repeatedly protrude and retract, respectively, which is likely to disturb the patient's sleep patterns or even wake-up the patient.

Applicant has discovered that OSA may be more effectively treated by targeting the Palatoglossus muscle PGM for electrical stimulation (e.g., rather than targeting the Genioglossus muscle GGM or the Hypoglossal nerve for electrical stimulation). More specifically, Applicant has discovered that application of one or more voltage differentials across selected portions of the patient's lateral or sublingual tissue may induce a current across the tongue to electrically stimulate the Palatoglossus muscle PGM in a manner that causes the Palatoglossus muscle PGM to shorten (e.g., to decrease its length). For at least some embodiments, the induced current may flow in a lateral direction across a base portion of the patient's tongue (e.g., proximate to the lateral points at which the Palatoglossus muscle inserts into the tongue T). Shortening the Palatoglossus muscle, using techniques described herein, may (1) stiffen and reduce the volume of the tongue T and (2) may cause the Palatoglossal arch PGA to pull down (e.g., in a downward direction) towards the base of the tongue T.

As described in more detail below, reducing the volume of the tongue T using techniques described herein may prevent the tongue T from prolapsing onto the back of the pharynx PHR, and pulling down the Palatoglossal arch PGA using techniques described herein may prevent the soft palate SP from collapsing onto the back of the pharynx PHR. In addition, stimulating the Palatoglossus muscle PGM using techniques described herein may also lower the superior surface SS of the tongue T, thereby causing the tongue to cinch downward (e.g., to "hunker down") in a manner that further prevents obstruction of the patient's upper airway.

Perhaps equally important, because the present embodiments do not target either the Hypoglossal nerve or the Genioglossus muscle GGM for electrical stimulation, the present embodiments may not cause the tongue T to move forward in the anterior direction during application of the electrical stimulation, which in turn may reduce the likelihood of undesirably waking-up the patient. Indeed, for at least some embodiments, the voltage differential may be applied across the patient's sublingual tissues in a manner that maintains the patient's tongue in a substantially stationary position while shortening the patient's Palatoglossus muscle PGM. In this manner, the present embodiments may maintain a patient's upper airway patency in a subtle yet therapeutic manner. Although electrical stimulation of the Palatoglossus muscle PGM using techniques described herein is not intended to stimulate the Genioglossus muscle GGM, any inadvertent stimulation of the Genioglossus muscle GGM will be relatively small and, at most, may serve to maintain the tongue T in a substantially stationary position.

Figure 2A:
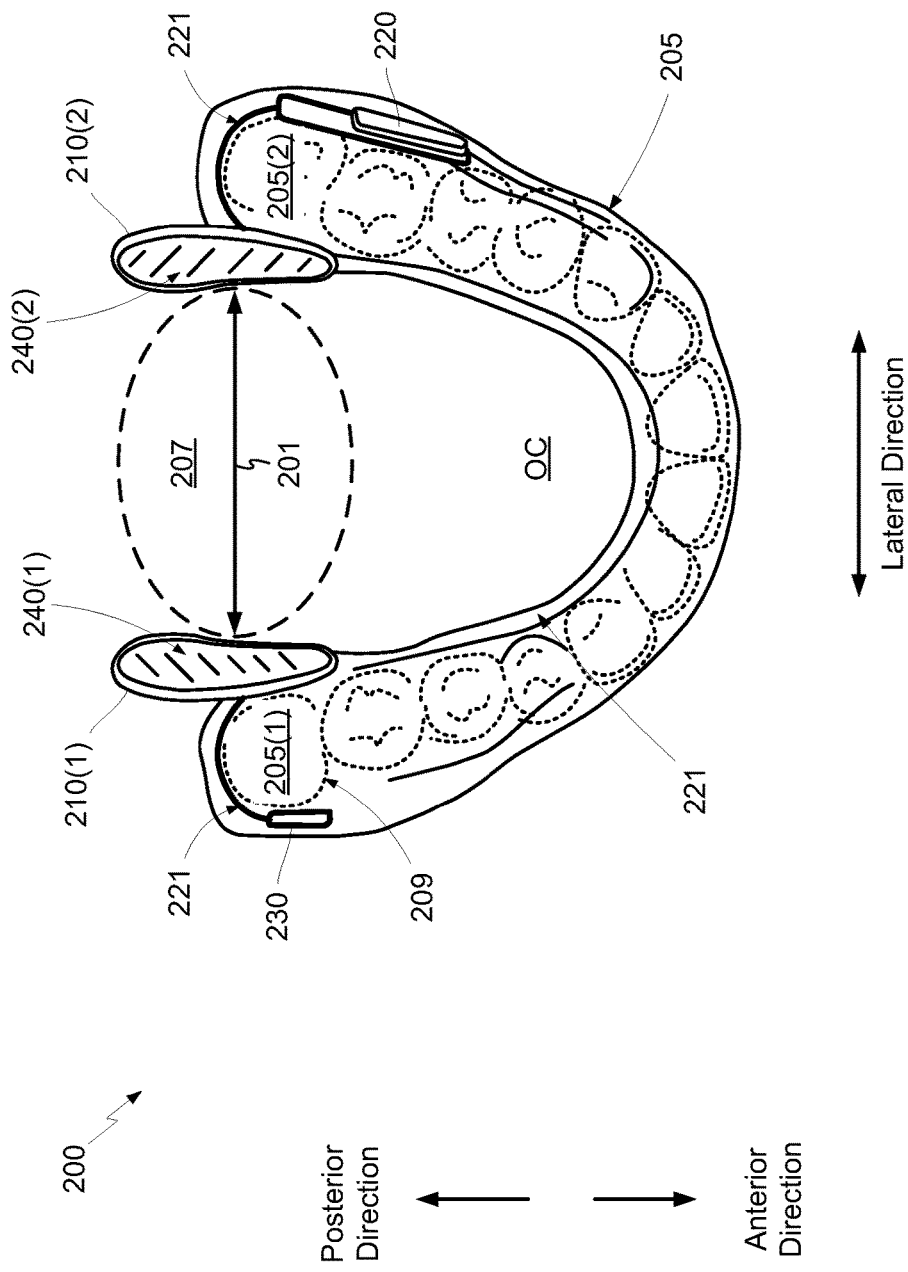
FIG. 2A is a top plan view of an oral appliance, situated over a patient's teeth, in accordance with some embodiments.
Figure 2B:
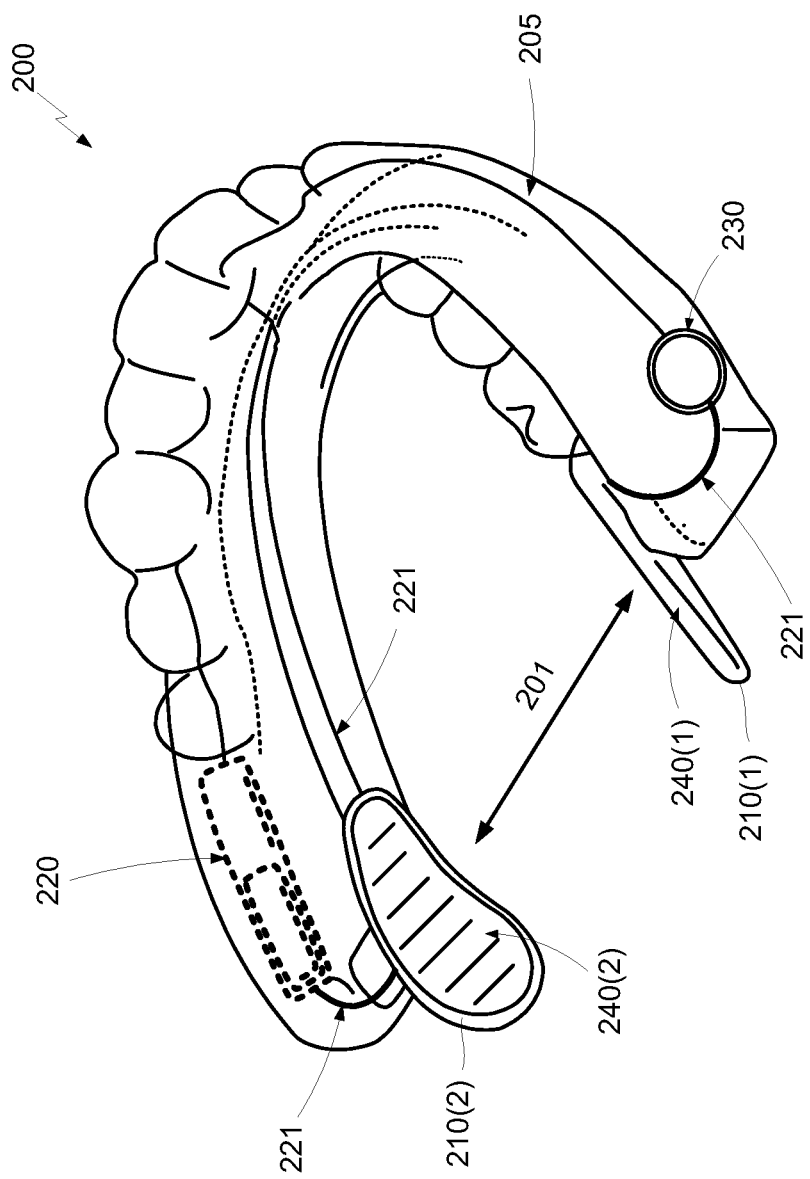
FIG. 2B is an elevated perspective view of the oral appliance of FIG. 2A.

FIGS. 2A-2B show a removable oral appliance 200 that, in accordance with at least some embodiments, may be used to treat OSA by using electrical stimulation of the Palatoglossus muscle PGM to prevent collapse, softening, or a reduction of muscle tone of the tongue T and soft palate SP into the back of the pharynx PHR or in the airway. The appliance 200 is shown in FIGS. 2A-2B as including an appliance body 205 upon which a number of electrodes 210(1)-210(2), a control circuit 220, and a power supply 230 may be mounted (or otherwise attached to) so as to form a unitary or divisible removable device that may fit generally within a patient's oral cavity OC (see also FIGS. 1A-1B). For such embodiments, there are no components external to the patient's body, and therefore the appliance 200 may not be associated with wires or other connectors that protrude from the patient's mouth or body. For some embodiments, the oral appliance 200 may be fitted over a patient's lower teeth and positioned to fit within a sublingual portion of the patient's oral cavity OC, for example, as depicted in FIG. 2A. For other embodiments, appliance 200 may be of other suitable configurations or structures, and the electrodes 210(1)-210(2) may be provided in other suitable positions. For some embodiments, there may be a minor portion of the oral appliance that protrudes slightly outside the lips or mouth.

Although only two electrodes 210(1)-210(1) are shown in FIGS. 2A-2B, it is to be understood that the appliance 200 may, in other embodiments, include a greater or fewer number of electrodes. For example, in other embodiments, the appliance 200 may include four or another number of electrodes 210 arranged in opposing (e.g., "X") patterns with respect to the patient's sublingual tissues, wherein pairs of the electrodes may be selectively enabled and disabled in a manner that alternately induces two or more currents across the patient's sublingual tissues. For such other embodiments, each of such electrodes may be turned on and/or off independently of the other electrodes, for example, to determine a pair (or more) of electrodes that, at a particular moment for the patient, correlate to optimum electrical stimulation. The determined pair of electrodes may be dynamically selected either by (1) directly correlating electrical stimulation and immediate respiratory response or by (2) indirectly using the oral appliance 200 "to look for" the lowest impedance electrode "pair(s)." The determined electrodes may or may not be at the ends of an "X" pattern, and may be opposing one another.

The first electrode 210(1) and/or the second electrode 210(2), which may be formed using any suitable material and may be of any suitable size and/or shape, are connected to the control circuit 220 by wires 221. The control circuit 220 and electrodes 210(1)-210(2) are electrically coupled to power supply 230 via wires 221. Note that the wires 221 may be positioned either within or on an outside surface of the appliance body 205, and therefore do not protrude into or otherwise contact the patient's tongue or oral tissue. The power supply 230 may be mounted in any of several locations and may be any suitable power supply (e.g., a battery) that provides power to control circuit 220 and/or electrodes 210(1)-210(2). Bi-directional gating techniques may be used to control voltages and/or currents within wires 221, for example, so that wires 221 may alternately deliver power to electrodes 210(1)-210(2) and exchange electrical signals (e.g., sensor signals) between electrodes 240(1)-240(2) and control circuit 220.

For the exemplary embodiment of FIGS. 2A-2B, the first electrode 210(1) may include or also function as a sensor 240(1), and the second electrode 210(2) may include or also function as a sensor 240(2), which could sense respiration or other functions of interest. In other words, for some embodiments, one or both of electrodes 210(1)-210(2) may also function as sensors such as respiration sensors. For such embodiments, the active function of the electrodes 210(1)-210(2) may be controlled using bi-directional gating techniques. For example, when the first electrode 210(1) is to function as a driven electrode, the bi-directional gating technique may connect the first electrode 210(1) to the output of a circuit such as a voltage and/or current driver (e.g., included within or associated with control circuit 220), for example, to provide a first voltage potential at the first electrode 210(1); conversely, when the first electrode 210(1) is to function as the respiration sensor or other sensor 240(1), the bi-directional gating technique may connect sensor 240(1) to the input of a circuit such as an amplifier and/or an ADC (analog to digital) converter (e.g., included within or associated with control circuit 220), for example, to sense a respiratory function of the patient. Similarly, when the second electrode 210(2) is to function as a driven electrode, the bi-directional gating technique may connect the second electrode 210(2) to the output of a circuit such as a voltage and/or current driver (e.g., included within or associated with control circuit 220), for example, to provide a second voltage potential at the second electrode 210(2); conversely, when the second electrode 210(2) is to function as the respiration sensor or other sensor 240(2), the bi-directional gating technique may connect sensor 240(2) to the input of a circuit such as an amplifier and/or an ADC (analog to digital) converter (e.g., included within or associated with control circuit 220), for example, to sense a respiratory function of the patient.

The respiration sensors or other sensors 240(1)-240(2), as provided within or otherwise associated with the electrodes 210(1)-210(2), may be any suitable sensors that measure any physical, chemical, mechanical, electrical, neurological, and/or other characteristics of the patient which may indicate or identify the presence and/or absence of disturbed breathing. These respiration sensors 240(1)-240(2) may also be used to detect snoring. For at least some embodiments, one or both of electrodes 210(1)-210(2) may include electromyogram (EMO) sensors that, for example, detect electrical activity of the muscles within, connected to, or otherwise associated with the patient's tongue T. For at least one embodiment, one or both of electrodes 210(1)-210(2) may include a microphone (or any other sensor to sense acoustic and/or vibration energy) to detect the patient's respiratory behavior. For other embodiments, one or both of electrodes 210(1)-210(2) may include one or more of the following non-exhaustive list of sensors: accelerometers, piezos, capacitance proximity detectors, capacitive sensing elements, optical systems, EMG sensors, etc.

For other embodiments, electrodes 210(1)-210(2) may not include any sensors. For at least one of the other embodiments, the electrodes 210(1)-210(2) may continuously provide electrical stimulation to the patient's Palatoglossus muscle PGM via the sublingual tissues. For an alternative embodiment, a timer (not shown for simplicity) may be provided on appliance body 205 or within control circuit 220 and configured to selectively enable/disable electrodes 210(1)-210(2), for example, based upon a predetermined stimulation schedule. In another closed-loop embodiment, the electrodes 210(1)-210(2) may be selectively enabled/disabled based upon one or more sources of sensor feedback from the patient.

For the exemplary embodiment of FIGS. 2A-2B, the first and second electrodes 210(1)-210(2) may be mounted on respective lateral arms 205(1) and 205(2) of the body 205 of appliance 200 such that when appliance 200 is placed within a sublingual portion of the patient's oral cavity OC, the first and second electrodes 210(1)-210(2) are positioned on opposite sides of the posterior sublingual region 207 of the patient's oral cavity OC. For other embodiments, the first and second electrodes 210(1)-210(2) may be separate from appliance body 205 but connected to respective lateral arms 205(1)-205(2), for example, so as to "float" beneath or on either side of the patient's tongue T, or alternatively oriented so as to be positioned on opposite sides of the superior surface of the tongue T. For some embodiments, the first and second electrodes 210(1)-210(2) are positioned in the posterior sublingual region 207 of the oral cavity OC such that at least a portion of each of the first and second electrodes 210(1)-210(2) is proximal to a molar 209 of the patient. In this manner, the first and second electrodes 210(1)-210(2) may be in physical contact with the patient's sublingual tissues proximate to the lateral posterior regions 101 at which the Palatoglossus muscle PGM inserts into the tongue T (see also FIGS. 1A-1B). Further, as depicted in FIGS. 2A-2B, the first and second electrodes 210(1)-210(2) may be angularly oriented with respect to the floor of the mouth such that the first and second electrodes 210(1)-210(2) substantially face and/or contact opposite sides of the tongue T proximate to the lateral posterior regions 101 at which the Palatoglossus muscle PGM inserts into the tongue T (see also FIGS. 1A-1B). For other embodiments, the first and second electrodes 210(1)-210(2) may be provided in one or more other positions and/or orientations.

The control circuit 220 may provide one or more signals to the first and second electrodes 210(1)-210(2) to create a voltage differential across the patient's sublingual tissues (e.g., across the base of the tongue) in the lateral direction. For purposes of discussion herein, the first electrode 210(1) may provide a first voltage potential V1, and the second electrode 210(2) may provide a second voltage potential V2. The voltage differential (e.g., V2−V1) provided between the first and second electrodes 210(1)-210(2) may induce a current 201 in a substantially lateral direction across the patient's sublingual tissues. For some embodiments, the current 201 is induced in a substantially lateral direction across the patient's tongue. The current 201, which for some embodiments may be a reversible current (as described in more detail below), electrically stimulates the patient's Palatoglossus muscle PGM in a manner that shortens the Palatoglossus muscle PGM.

When the Palatoglossus muscle PGM is stimulated and/or shortened in response to the current 201 induced by the first and second electrodes 210(1)-210(2), the Palatoglossus muscle PGM causes the tongue T to stiffen in a manner that decreases the tongue's volume, and that may also slightly cinch a portion of the tongue T closer to the floor of the oral cavity OC. One or more of decreasing the tongue's volume and slightly cinching the tongue T downward towards the floor of the oral cavity OC may prevent the tongue T from prolapsing onto the back of the pharynx PHR, thereby maintaining patency of the patient's upper airway (e.g., without moving the tongue forward in the anterior direction). The shortening of the Palatoglossus muscle PGM may also pull the patient's Palatoglossal arch PGA in a downward direction towards the base of the tongue T, which in turn may prevent the soft palate SP from collapsing and obstructing the patient's upper airway.

Figure 3A:
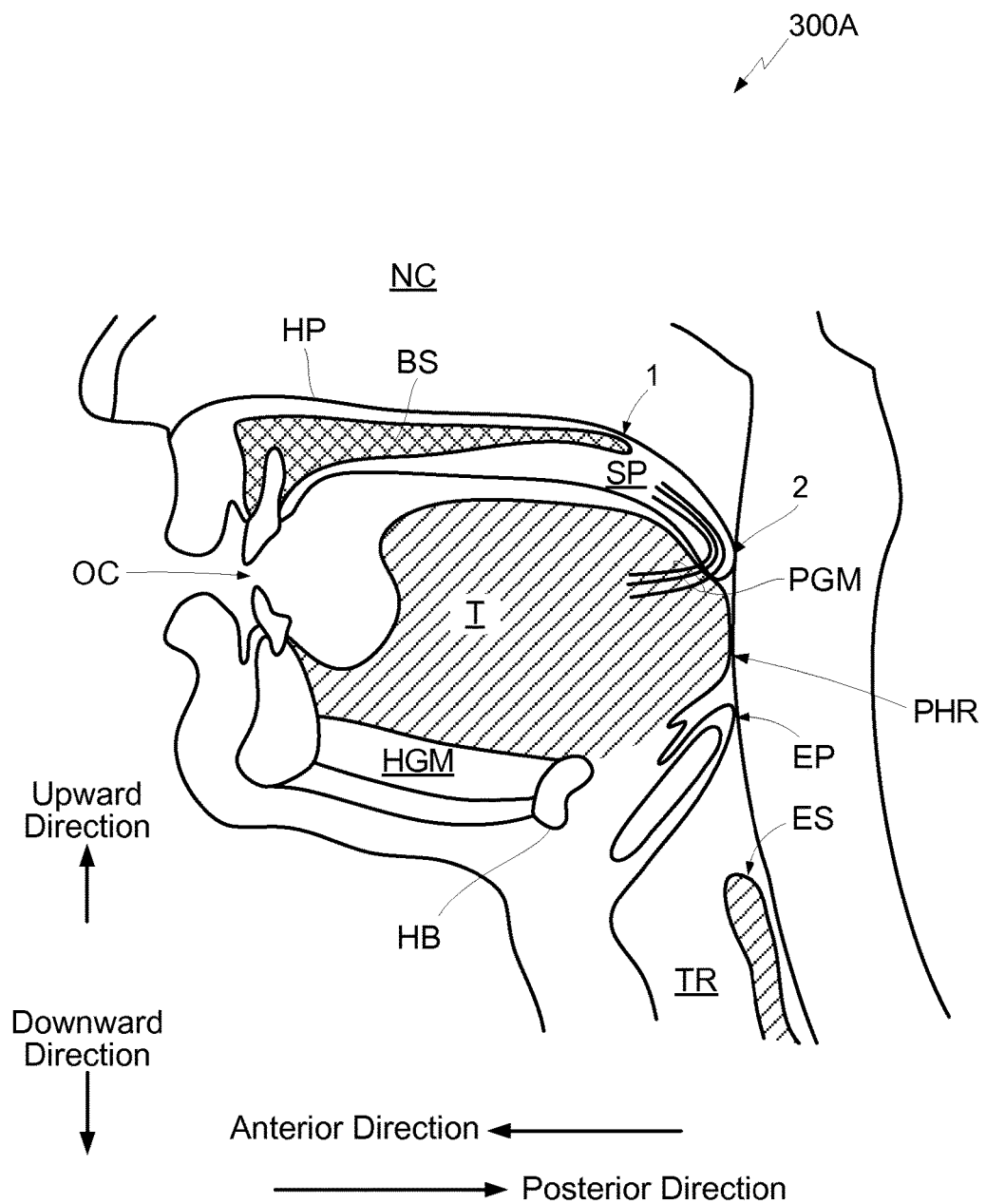
FIG. 3A is a side sectional view depicting a patient's upper airway during disturbed breathing.

For example, FIG. 3A shows a side view 300A of a patient depicting the collapse of the patient's tongue T and soft palate SP in a posterior direction towards the back of the pharynx (PHR) during disturbed breathing. As depicted in FIG. 3A, the patient's upper airway is obstructed by the tongue T prolapsing onto the back wall of the pharynx PHR and/or by the soft palate SP collapsing onto the back wall of the pharynx PHR.

Figure 3B:
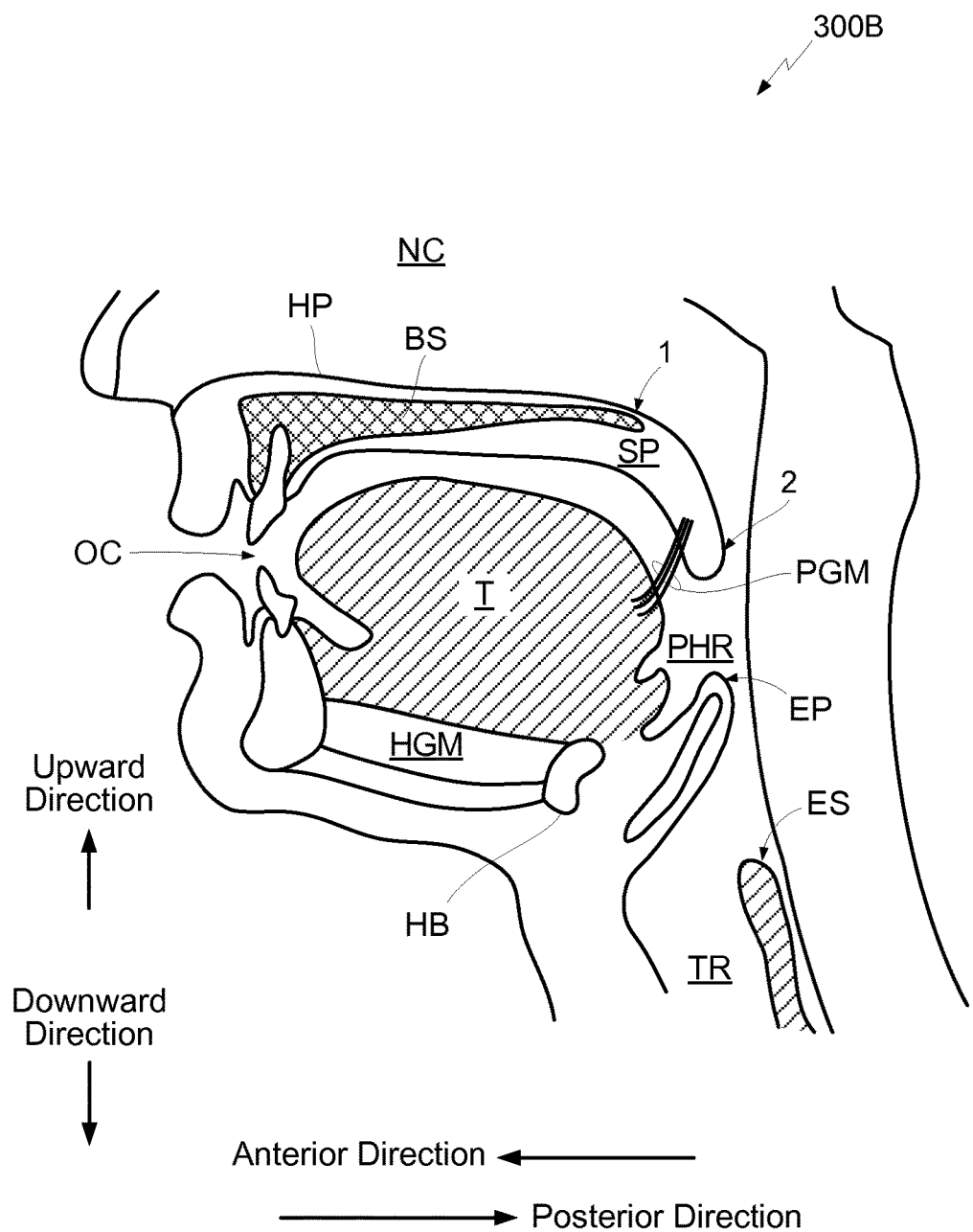
FIG. 3B is a side sectional view depicting the patient's upper airway response to electrical stimulation provided in accordance with the present embodiments.

In contrast, FIG. 3B shows a side view 300B of the patient depicting the patient's upper airway response to electrical stimulation provided in accordance with the present embodiments. More specifically, electrical stimulation provided by one or more embodiments of the appliance 200 may cause the Palatoglossus muscle PGM to stiffen and shorten, which in turn may pull the patient's soft palate SP and/or palatal arches in a downward direction, thereby preventing the soft palate SP from collapsing onto the back wall of the pharynx PHR. In addition, stiffening and/or shortening the Palatoglossus muscle PGM may also cause the patient's tongue T to contract and/or cinch downward in a manner that prevents collapse of the tongue T towards the back of the pharynx PHR without substantially moving the tongue T forward in the anterior direction.

The control circuit 220 may be any suitable circuit or device (e.g., a processor) that causes electrical stimulation energy to be provided to areas proximate to the base of the patient's tongue T via the electrodes 210(1)-210(2). More specifically, the control circuit 220 may generate one or more voltage waveforms that, when provided as signals and/or drive signals to the first and second electrodes 210(1)-210(2), primarily induces a current across (e.g., in a substantially lateral direction) the sub-lingual portion of the patient's tongue T in a manner that causes the patient's Palatoglossus muscle PGM to shorten. The waveforms provided by control circuit 220 may include continuous voltage waveforms, a series of pulses, or a combination of both. The control circuit 220 may be formed using digital components, analog components, or a combination of analog and digital components.

For some embodiments, the control circuit 220 may vary or modify the waveform in a manner that induces a reversible current across the sublingual portion of the patient's tongue T (e.g., across the base of the tongue). Applicant has discovered that inducing a reversible current across the sublingual portion of the tongue T may decrease the likelihood of patient discomfort (e.g., as compared with providing a constant current or current in a single direction). More specifically, Applicant notes that when a current is induced in the sublingual tissues of the patient, the sublingual tissues may experience carrier depletion, which in turn may require greater voltage differentials and/or greater current magnitudes to maintain a desired level of electrical stimulation of the Palatoglossus muscle PGM. However, inducing greater voltage and/or current magnitudes to offset increasing levels of carrier depletion may create patient discomfort. Thus, to prevent carrier depletion of the patient's sublingual tissues, the control circuit 220 may limit the duration of pulses that induce the current 201 across the sublingual tissues and/or may from time to time reverse the direction (e.g., polarity) of the current 201 induced across the patient's sublingual tissues.

For some embodiments, control circuit 220 may generate and/or dynamically adjust the waveform and/or drive waveform provided to the first and second electrodes 210(1)-210(2) in response to one or more input signals indicative of the patient's respiratory behavior and/or inputs from other characteristics and sensing methods. The input signals may be provided by one or more of the sensors 240(1)-240(2) integrated within respective electrodes 210(1)-210(2).

Figure 2C:
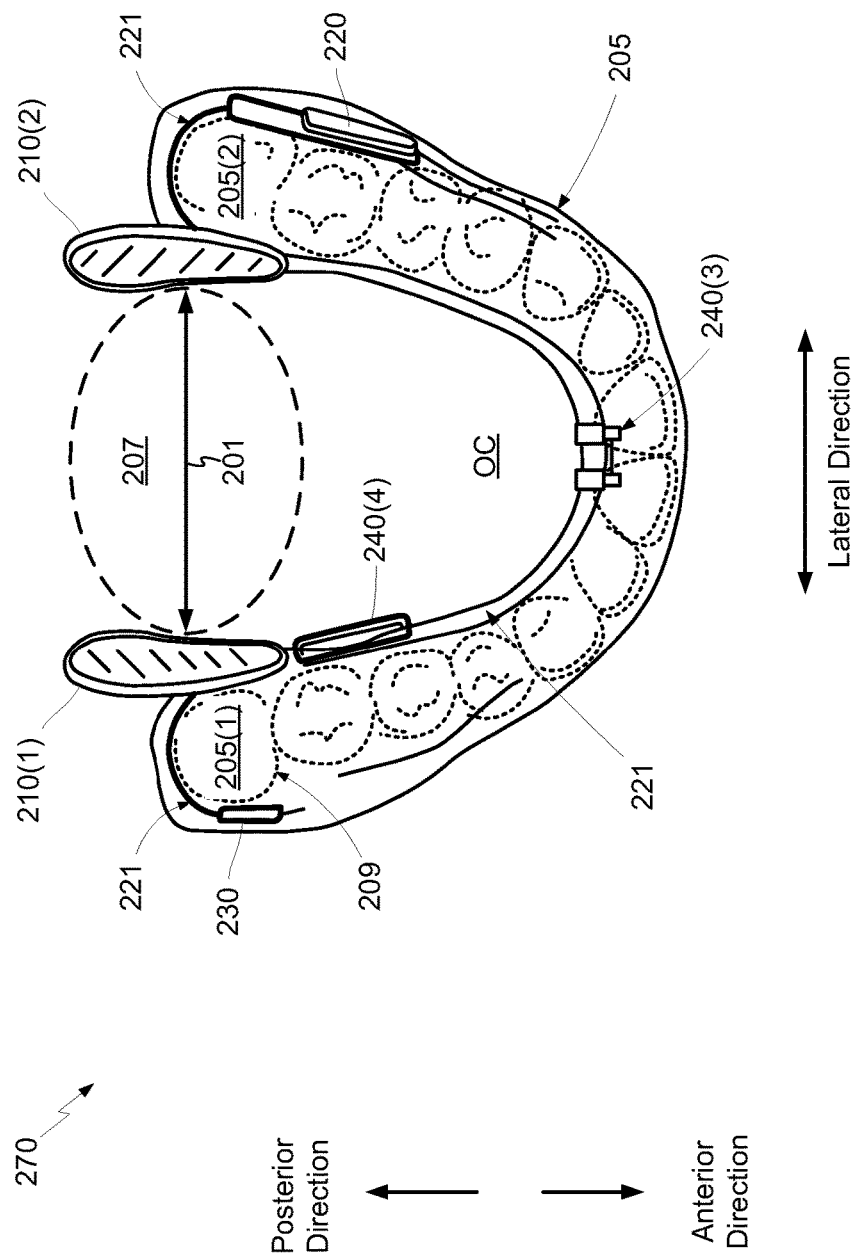
FIG. 2C is a top plan view of an oral appliance, situated over a patient's teeth, in accordance with other embodiments.
Figure 2D:
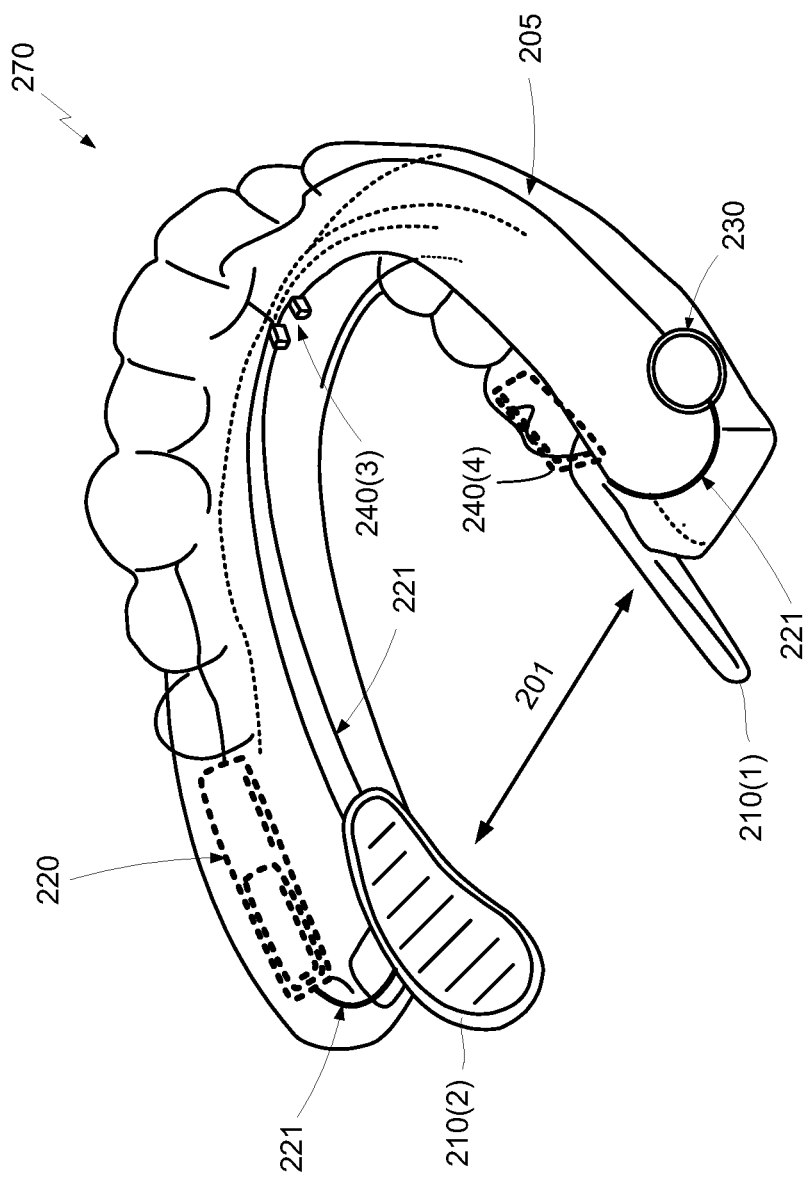
FIG. 2D is an elevated perspective view of the oral appliance of FIG. 2C.

For other embodiments, sensors other than the sensors 240(1)-240(2) integrated within respective electrodes 210(1)-210(2) may be used to generate the input signals. For example, FIGS. 2C-2D show a removable oral appliance 270 in accordance with other embodiments. Appliance 270 may include all the elements of the appliance 200 of FIGS. 2A-2B, plus additional sensors 240(3)-240(4). For the exemplary embodiment of FIGS. 2C-2D, the sensor 240(3) may be an oxygen saturation ($O_2$ sat) sensor that provides a signal indicative of the patient's oxygen saturation level, and the sensor 240(4) may be a vibration sensor that provides a signal indicative of the patient's respiratory activity (as measured by vibrations detected within the patient's oral cavity). For other embodiments, sensors 240(3)-240(4) may be other types of sensors including, for example, sensors that measure air composition (especially $O_2$ and $CO_2$), heart rate, respiration, temperature, head position, snoring, pH levels, and others.

Figure 4:
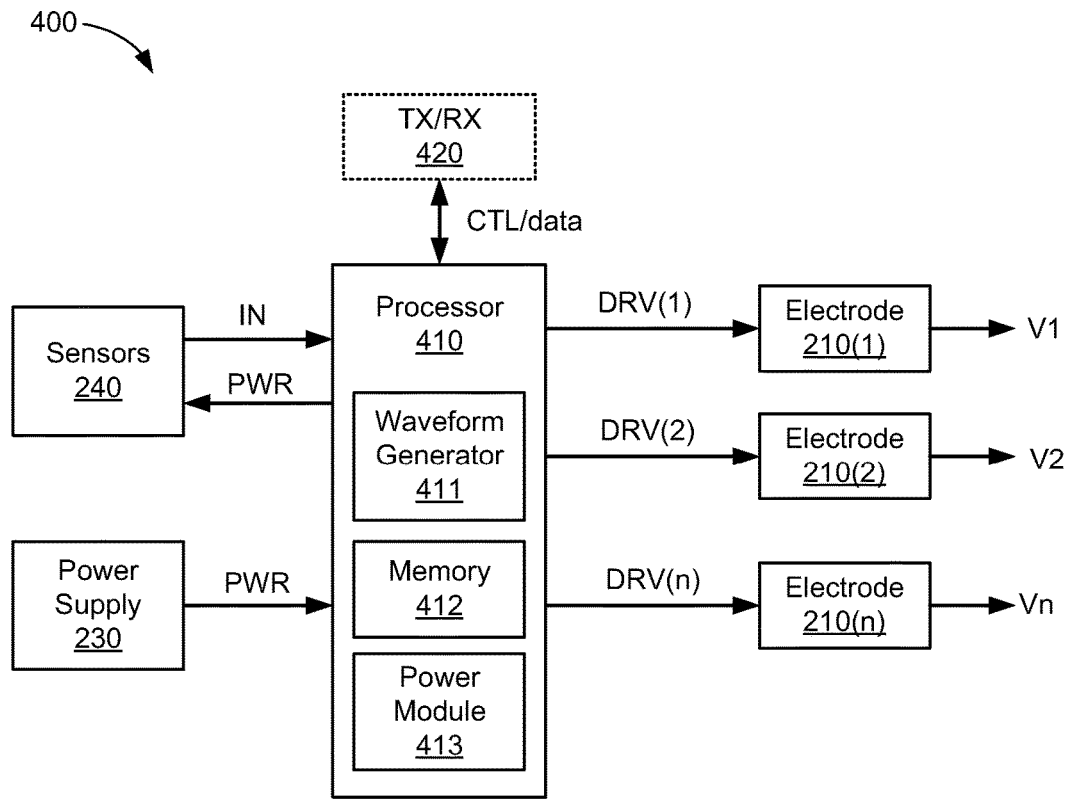
FIG. 4 is a block diagram of the electrical components of the oral appliance of FIGS. 2A-2B.

FIG. 4 shows a block diagram of the electrical components of an appliance 400 that is one embodiment of the appliance 200 of FIGS. 2A-2B. Appliance 400 is shown to include a processor 410, a plurality of electrodes 210(1)-210(n), power supply 230, sensors 240, and an optional transceiver 420. Processor 410, which is one embodiment of the control circuit 220 of FIGS. 2A-2B, includes a waveform generator 411, a memory 412, and a power module 413. The power supply 230, which as mentioned above may be any suitable power supply (e.g., a battery), provides power (PWR) to processor 410. For some embodiments, the processor 410 may use power module 413 to selectively provide power to sensors 240, for example, only during periods of time that the sensors 240 are to be active (e.g., only when it is desired to receive input signals from sensors 240). Selectively providing power to sensors 240 may not only reduce power consumption (thereby prolonging the battery life of power supply 230) but may also minimize electrical signals transmitted along wires 221 to the processor 410. For other embodiments, power supply 230 may provide power directly to sensors 240.

The sensors 240, which may include sensors 240(1)-240(2) of FIGS. 2A-2B and/or sensors 240(3)-240(4) of FIGS. 2C-2D, may provide input signals to processor 410. The input signals may be indicative of the respiratory behavior or other functions of the patient and may be used to detect the presence and/or absence of disturbed breathing, for example, as described above with respect to FIGS. 2A-2D.

The processor 410 may receive one or more input signals from sensors 240, or sensors located elsewhere, and in response thereto may provide signals and/or drive signals (DRV) to a number of the electrodes 210(1)-210(n). As described above, the signals and/or drive signals (e.g., voltage and/or current waveforms) generated by waveform generator 411 may cause one or more of the electrodes 210(1)-210(n) to electrically stimulate sublingual portions of the patient's oral cavity OC in a manner that shortens the patient's Palatoglossus muscle PGM. Shortening the Palatoglossus muscle PGM in response to electrical stimulation provided by one or more of the electrodes 210(1)-210(n) may (1) stiffen and reduce the volume of the tongue T, (2) may cause the tongue to cinch downward, and (3) may cause the Palatoglossal arch PGA to pull down (e.g., in a downward direction) towards the base of the tongue T. In this manner, the electrical stimulation provided by the one or more electrodes 210(1)-210(n) may prevent the tongue T from prolapsing onto the back of the pharynx PHR and/or may prevent the soft palate SP from collapsing onto the back of the pharynx PHR.

As mentioned above, the waveforms generated by the waveform generator 411, when provided as signals and/or drive signals to the electrodes 210(1)-210(n), primarily induce a current across the patient's sub-lingual tissues in a manner that causes the patient's Palatoglossus muscle PGM to shorten. The waveforms generated by the waveform generator 411 may include continuous (analog) voltage waveforms, any number of pulses that may vary in shape and duration as a pulse train, or the pulses may be combined to simulate an analog waveform or a combination of both, and may be dynamically modified by the waveform generator 411.

The optional transceiver 420 may be used to transmit control information (CTL) and/or data, and/or receive control information and/or data from an external device via a suitable wired or wireless connection. The external device (not shown for simplicity) may be any suitable display device, storage device, distribution system, transmission system, and the like. For one example, the external device may be a display (e.g., to display the patient's respiratory behavior or patterns, to alert an observer to periods of electrical stimulation, to indicate an alarm if breathing stops, and so on).

For another example, the external device may be a storage device that stores any data produced by appliance 200, perhaps including the patient's respiratory behavior, the electrical stimulation provided by appliance 200, the waveforms provided by waveform generator 411, and/or relationships between two or more of the above. More specifically, for some embodiments, the external device may store data for a plurality of patients indicating, for example, a relationship between the application of electrical stimulation to the patient and the patient's respiratory response to such electrical stimulation, and may include other information. Such relationship data for large numbers of patients may be aggregated, and thereafter used to identify trends or common components of OSA across various population demographics. The storage device may be a local storage device, or may be a remote storage device (e.g., accessible via one or more means and/or networks including but not limited to such as a wide area network (WAN), a wireless local area network (WLAN), a virtual private network (VPN), and/or the Internet). The data and information may be made available and/or manipulated locally and/or remotely, and may be utilized immediately and/or preserved for later utilization and/or manipulation.

Memory 412 may include a non-transitory computer-readable storage medium (e.g., one or more nonvolatile memory elements, such as EPROM, EEPROM, Flash memory, a hard drive, etc.) that may store the following software modules and/or information:
  a function select module to selectively switch an active function of the electrodes 210 between an electrode mode (e.g., provided by one or more of electrodes 210 and a sensor mode (e.g., provided by one or more of sensors 240);
  a control module to selectively provide signals and/or drive signals to the electrodes 210, for example, to induce an electric current across a portion of the patient's oral cavity in accordance with the present embodiments and/or to receive input signals from the sensors 240; and
  a data collection module to record data indicative of the patient's respiratory or other behavior and/or to transmit such data to an external device.

Each software module may include instructions that, when executed by the processor 410, may cause appliance 400 to perform the corresponding function. Thus, the non-transitory computer-readable storage medium of memory 412 may include instructions for performing all or a portion of the operations described below with respect to FIG. 6. The processor 410 may be any suitable processor capable of executing scripts of instructions of one or more software programs stored in the appliance 400 (e.g., within memory 412). For at least some embodiments, memory 412 may include or be associated with a suitable volatile memory, for example, to store data corresponding to the patient's respiratory functions and/or corresponding to the electrical stimulation provided by the appliance 200.

Figure 5:
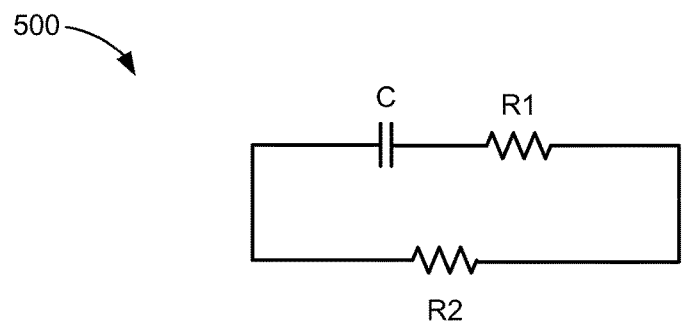
FIG. 5 is a circuit diagram illustrating an electrical model of the patient's tongue.

As mentioned above, the control circuit 220 may control the duration of pulses that induce the current 201 across the patient's sublingual tissues, for example, to minimize carrier depletion within the patient's sublingual tissues and/or may from time to time reverse the direction of the induced current 201, for example, to provide a zero sum drive waveform (e.g., to minimize or preclude electrochemical activity and/or or to minimize the patient's awareness of any electrical activity related to oral appliance 200). For at least one embodiment, the control circuit 220 may select the pulse lengths based upon a resistive-capacitive (RC) time constant model of the patient's tongue T. For example, FIG. 5 shows an RC time constant model 500 of the patient's tongue T. The model 500 is shown to include a capacitor C and two resistors, R1 and R2. For an exemplary embodiment, the capacitor C may be approximately 0.5 uF, the resistor R1 may be approximately 600 ohms, and the resistor R2 may be approximately 4,000 ohms. Thus, for the exemplary embodiment, the time constant $\tau=R1*C$ may be a value approximately equal to 300 µs. The resistor R2 represents minor "DC current" flow in the model, where the current stabilizes at a small but non-zero value after more than 5 time constants or when DC is applied to the electrodes.

More specifically, Applicant has discovered that a typical patient's tongue T is most receptive to a current "pulse duration" that is equal to or shorter than a time period approximately equal to $\tau=R1*C\approx300$ µs. After the time period at $3\tau\approx1$ ms expires, the patient's tongue T may exhibit an even greater increase in impedance, or perhaps experience carrier depletion, which in turn requires greater voltage levels to continue inducing the current 201 across the patient's sublingual tissues. As noted above, increasing the voltage levels to continue inducing the current 201 across the patient's sublingual tissues may not only waste battery or wired power but also may cause discomfort (or even pain) to the patient. Indeed, because current regulators typically utilize their available voltage "headroom" to increase the drive voltage and maintain a constant current flow when the load impedance increases or when the effective drive voltage otherwise decreases, it is important to dynamically manage the effective drive voltage provided by the electrodes 210(1)-210(2).

The effective drive voltage may decrease when there is an increased impedance, or perhaps carrier depletion, in the patient's tongue, and the drive resistance may increase when one (or both) of the electrodes 210(1)-210(2) loses contact with the patient's sublingual tissues, generally causing the control circuit 220 to increase its drive voltage in an attempt to maintain a prescribed current flow. Thus, for at least some embodiments, the control circuit 220 may be configured to limit the drive voltage and/or the current to levels that are known to be safe and comfortable for the patient, even if the drive impedance becomes unusually high. In addition, the control circuit 220 may be configured to from time to time reverse the polarity or direction of the induced current 201. The reversal of the current 201 can be performed at any time. The timing of the reversal of current 201 may be selected such that there is no net transfer of charge across the patient's sublingual tissues (e.g., a zero sum waveform).

Figure 6:
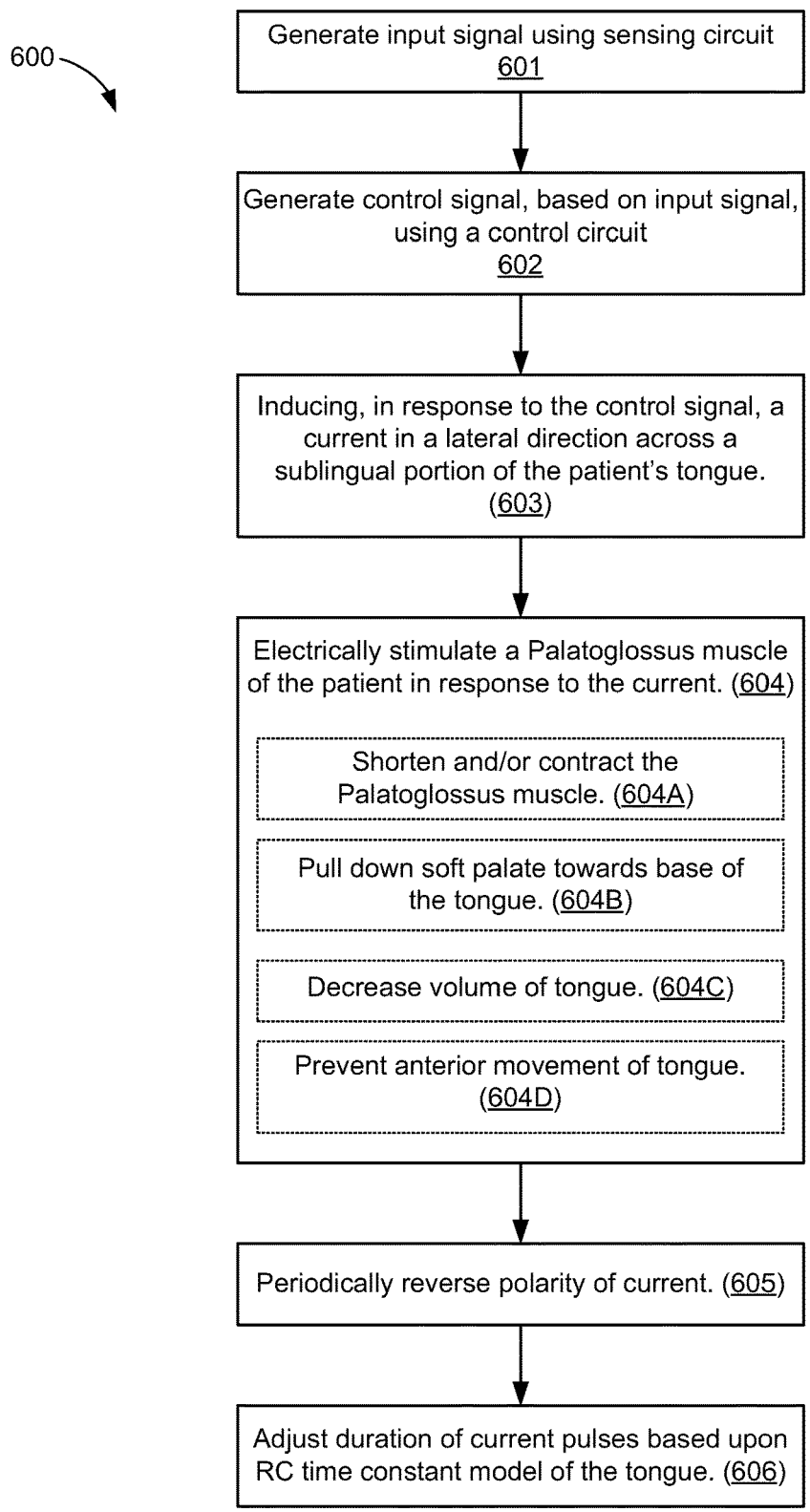
FIG. 6 is an illustrative flow chart depicting an exemplary operation in accordance with some embodiments.
Figure 7A:
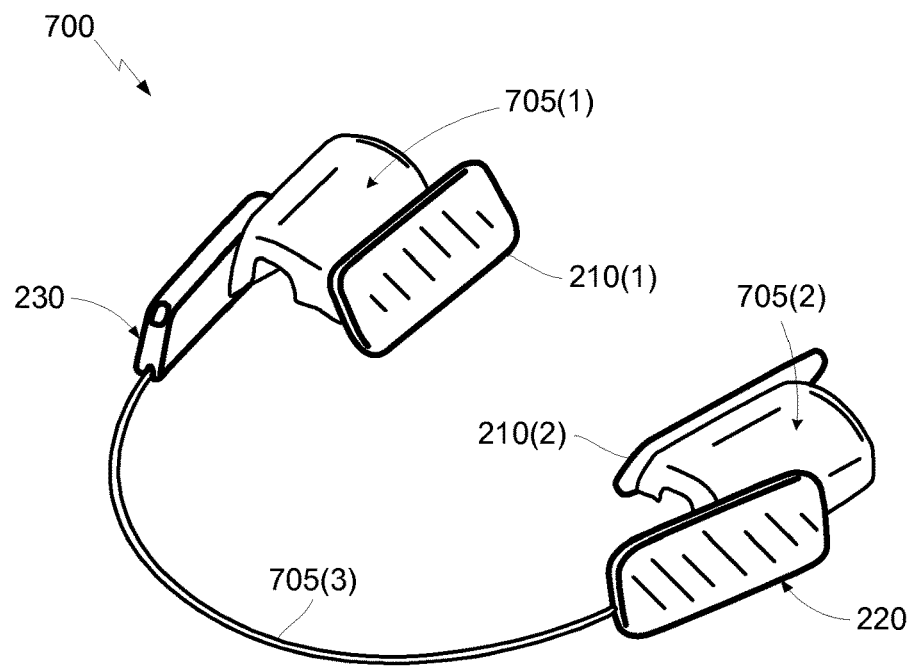
FIG. 7A is an elevated perspective view of an oral appliance in accordance with other embodiments.
Figure 7B:
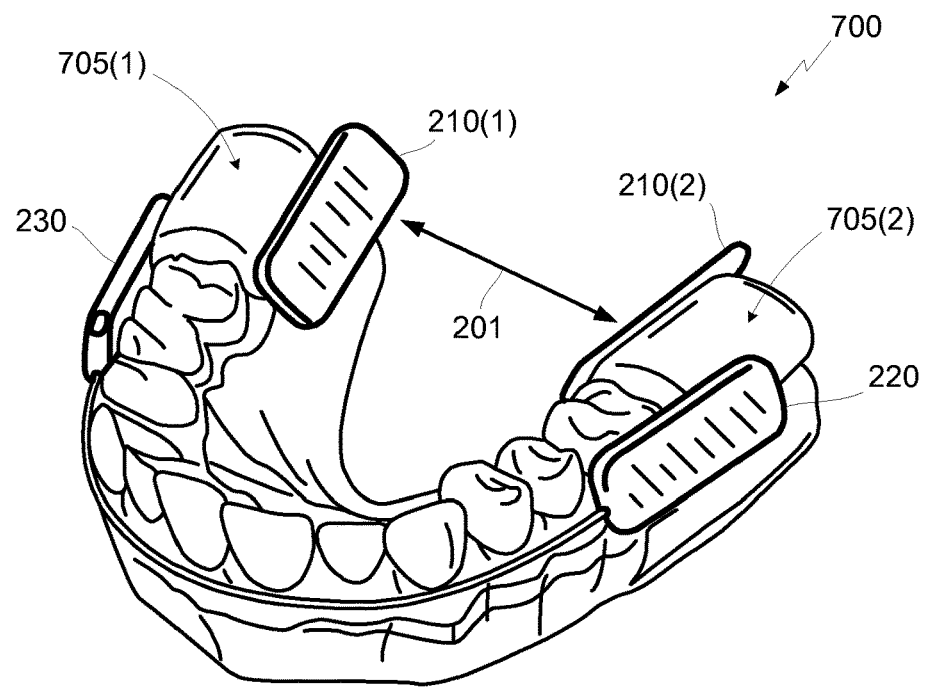
FIG. 7B is an elevated perspective view of the oral appliance of FIG. 7A situated over a patient's teeth.
Figure 7C:
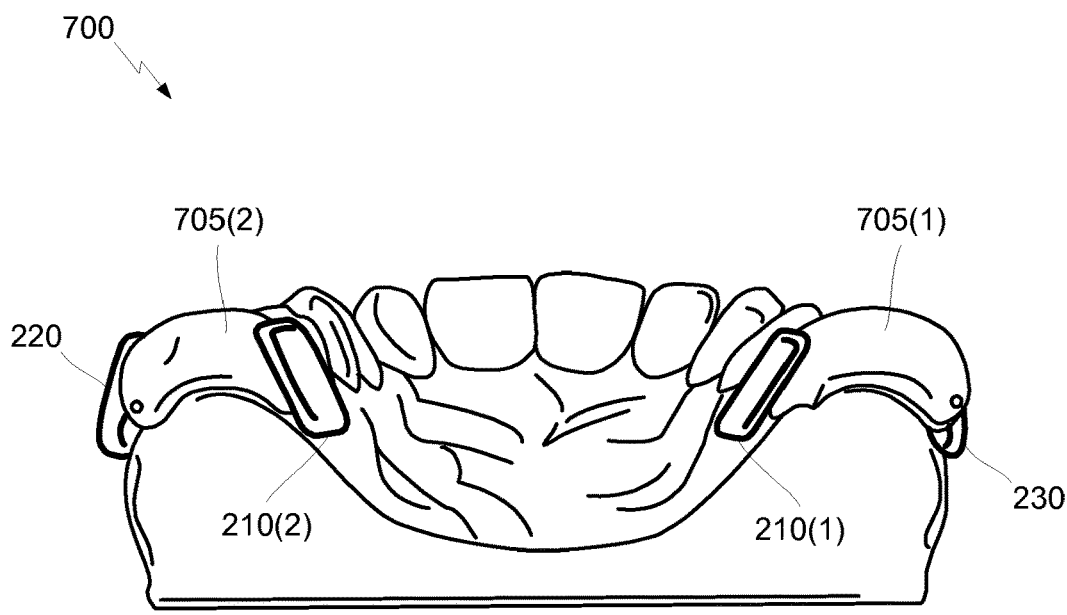
FIG. 7C is a rear plan view of the oral appliance of FIG. 7A situated over a patient's teeth.
Figure 7D:
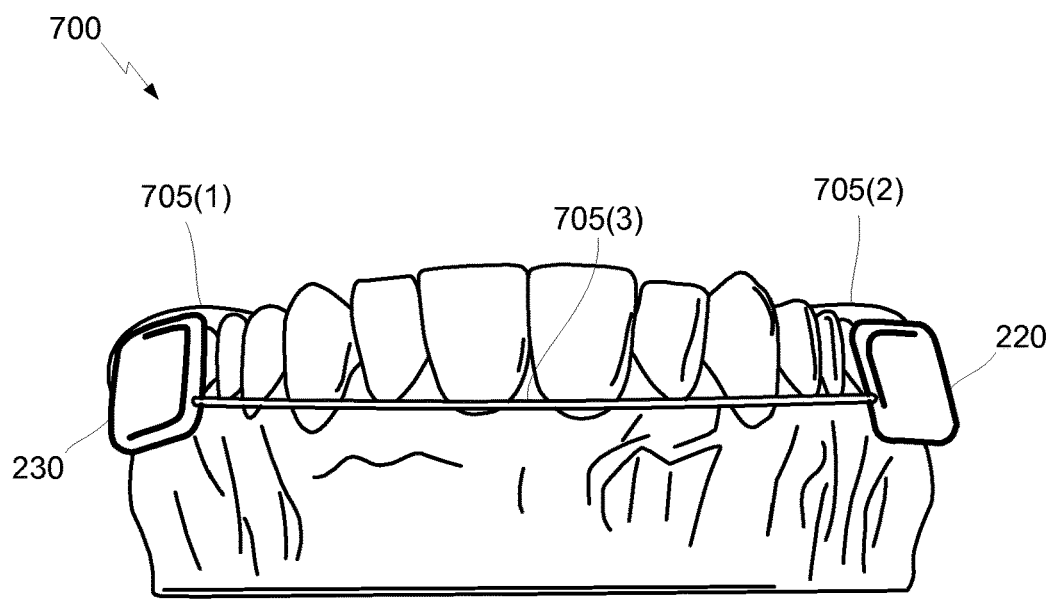
FIG. 7D is a front plan view of the oral appliance of FIG. 7A situated over a patient's teeth.

FIG. 6 is a flow chart 600 depicting an exemplary operation for providing electrical stimulation to a patient in accordance with the present embodiments. Although the flow chart 600 is discussed below with respect to appliance 200 of FIGS. 2A-2B, the flow chart 600 is equally applicable to other embodiments discussed herein. Prior to operation, the appliance 200 is positioned within a sublingual portion of the patient's oral cavity, for example, so that the electrodes 210(1)-210(2) are positioned on opposite sides of the patient's tongue proximate to the lateral posterior regions 101 at which the Palatoglossus muscle PGM inserts into the tongue T (see also FIGS. 1A-1B). Once the appliance 200 is properly fitted within the patient's oral cavity, the appliance 200 accepts zero or more input signals using a number of sensing circuits provided on or otherwise associated with appliance 200 (601). As discussed above, the input signals may be indicative of the respiratory state or other behavior of the patient, and may be derived from or generated by any suitable sensor. The control circuit 220 generates a number of control and/or drive signals based on the input signals. (602).

In response to the signals and/or drive signals, the electrodes 210(1)-210(2) induce a current in a lateral direction across a sublingual portion of the patient's tongue (603). The current induced across the sublingual portion of the patient's tongue electrically stimulates the patient's Palatoglossus muscle (604). As described above, electrically stimulating the patient's Palatoglossus muscle may shorten the Palatoglossus muscle (604A), may pull down the patient's soft palate towards the base of the tongue (604B), may decrease the volume of the tongue (604C), and/or may prevent anterior movement of the tongue (604D).

For some embodiments, the induced current may be a reversible current. For at least one embodiment, the reversible current may be a zero-sum waveform. For such embodiments, the control circuit 220 may from time to time reverse a polarity of the reversible current (605), and/or may adjust the duration and/or amplitude of voltage and/or current pulses and/or waveforms based on the RC time constant model of the patient's tongue (606).

FIGS. 7A-7D show a removable oral appliance 700 in accordance with other embodiments. The oral appliance 700, which may be used to treat OSA by providing electrical stimulation to a patient's sublingual tissues in a manner that causes the Palatoglossus muscle to shorten, is shown to include an appliance body 705 (which includes portions 705(1)-705(3), as shown in one or more of FIGS. 7A-7D) upon which electrodes 210(1)-210(2), control circuit 220, and power supply 230 may be mounted (or otherwise attached to) so as to form a unitary and removable device that may fit entirely within a patient's oral cavity OC (see also FIGS. 1A-1B). The oral appliance 700, which may operate in a similar manner as the oral appliance 200 of FIGS. 2A-2B, includes appliance body 705 instead of appliance body 205 of FIGS. 2A-2B. Specifically, appliance body 705 includes two anchor portions 705(1)-705(2) and a support wire 705(3). The anchor portions 705(1)-705(2) may be fitted over opposite or approximately opposite molars of the patient, with the support wire 705(3) connected between anchor portions 705(1)-705(2) and extending along the patient's gum line.

More specifically, for the exemplary embodiments described herein, the first electrode 210(1) may be attached to or otherwise associated with the first anchor portion 705(1), and the second electrode 210(2) may be attached to or otherwise associated with the second anchor portion 705(2). The control circuit 220 may be attached to support wire 705(3) and/or the second anchor portion 705(2), and the power supply 230 may be attached to support wire 705(3) and/or the first anchor portion 705(1) and/or the second anchor portion 705(2). Wires 221 (not shown in FIGS. 7A-7D for simplicity) may be attached to or provided within the support wire 705(3).

In the foregoing specification, the present embodiments have been described with reference to specific exemplary embodiments thereof. It will, however, be evident that various modifications and changes may be made thereto without departing from the broader scope of the disclosure as set forth in the appended claims. The specification and drawings are, accordingly, to be regarded in an illustrative sense rather than a restrictive sense.

What is claimed is:
1. A device configured to provide electrical stimulation to an oral cavity of a patient, the device comprising:
an appliance including a body having first and second lateral arms each terminating in a posterior-most free end;

a first electrode including a first portion directly attached to a lingual side of the posterior-most free end of the first lateral arm and including a second portion extending posteriorly beyond the posterior-most free end of the first lateral arm;

a second electrode including a first portion directly attached to a lingual side of the posterior-most free end of the second lateral arm and including a second portion extending posteriorly beyond the posterior-most free end of the second lateral arm, wherein the first and second electrodes are configured to be angularly oriented with respect to a floor of the patient's mouth such that the first and second electrodes are adapted to face opposite lateral sides of the patient's tongue; and a control circuit coupled to the appliance and to the electrodes, the control circuit configured to induce a current in a lateral direction across the tongue via the first and second electrodes to generate the electrical stimulation.

2. The device of claim 1, wherein at least one of the electrodes is further configured to sense a respiration function of the patient.

3. The device of claim 2, wherein the control circuit is further configured to:

provide one or more first signals to the at least one of the electrodes during a first mode, the one or more first signals configured to induce the current; and receive a second signal from the at least one of the electrodes during a second mode, the second signal indicative of the patient's respiration function.

4. The device of claim 3, wherein the control circuit is further configured to dynamically adjust the one or more first signals in response to the second signal.

5. The device of claim 1, wherein the induced current comprises one or more reversible currents configured to flow in one or more substantially lateral directions across the tongue.

6. The device of claim 5, wherein at least one of the reversible currents comprises a zero-sum waveform.

7. The device of claim 5, wherein a pulse length of at least one of the reversible currents is configured according to a resistive-capacitive (RC) time constant model associated with the tongue.

8. The device of claim 1, further comprising:

a power supply, mounted on the appliance, to provide power to the control circuit.

9. The device of claim 8, wherein the appliance, the electrodes, the control circuit, and the power supply comprise a unitary device adapted to fit entirely within the patient's oral cavity.

10. The device of claim 1, wherein the electrodes are configured to induce the current by providing a voltage differential across the tongue.

11. The device of claim 1, wherein the first and second electrodes are adapted to be in contact with opposite sides of the patient's tongue proximate to lateral points at which a Palatoglossus muscle inserts into the tongue when the appliance is inserted within the oral cavity.

12. The device of claim 1, wherein the electrodes are responsive to one or more signals generated by the control circuit.

13. The device of claim 1, wherein the induced current is configured to shorten the patient's Palatoglossus muscle without targeting the patient's Hypoglossal nerve.

14. The device of claim 1, wherein the induced current is configured to pull the patient's Palatoglossal arch in a downward direction towards a base of the tongue.

15. The device of claim 1, wherein the induced current is configured to decrease a volume of the tongue without moving the tongue in an anterior direction.

16. The device of claim 1, wherein one or more of the electrodes comprises an electromyogram (EMG) sensor configured to detect electrical activity of muscles within or connected to the patient's tongue.

17. The device of claim 1, wherein the electrical stimulation is configured to avoid targeting a genioglossus muscle of the patient.

18. The device of claim 1, wherein the electrical stimulation is configured to avoid targeting a hypoglossal nerve of the patient.

19. The device of claim 1, wherein the device is removable.

20. The device of claim 1, wherein at least one of the electrodes is further configured to detect snoring in the patient.

21. The device of claim 1, wherein at least a portion of each of the first and second electrodes is adapted to be positioned posterior to a last molar location of the patient when the appliance is inserted within the oral cavity.

22. An appliance adapted to fit at least partially within and configured to provide electrical stimulation to a patient's oral cavity, the appliance comprising:

a body having first and second lateral arms each terminating in a posterior-most free end;

a first electrode including a first portion directly attached to a lingual side of the posterior-most free end of the first lateral arm and including a second portion extending posteriorly beyond the posterior-most free end of the first lateral arm;

a second electrode including a first portion directly attached to a lingual side of the posterior-most free end of the second lateral arm and including a second portion extending posteriorly beyond the posterior-most free end of the second lateral arm, wherein the first and second electrodes are configured to be angularly oriented with respect to a floor of the patient's mouth such that the first and second electrodes are adapted to contact opposite sublingual sides of the patient's tongue proximate to lateral points at which a Palatoglossus muscle inserts into the tongue; and a control circuit coupled to the appliance and to the electrodes, the control circuit configured to induce a current in a lateral direction across the tongue via the first and second electrodes to generate the electrical stimulation.

23. The appliance of claim 22, wherein at least one of the electrodes is further configured to sense a respiration function of the patient.

24. The appliance of claim 23, wherein the control circuit is further configured to:

provide one or more first signals to the at least one of the electrodes during a first mode; and receive a second signal from the at least one of the electrodes during a second mode, the second signal indicative of the patient's respiration function.

25. The appliance of claim 24, wherein the control circuit is further configured to dynamically adjust the one or more first signals in response to the second signal.

26. The appliance of claim 22, wherein the induced current comprises a reversible current.

27. The appliance of claim 26, wherein the reversible current is configured to decrease a volume of the tongue.

28. The appliance of claim 26, wherein the reversible current comprises a zero-sum waveform.

29. The appliance of claim 26, wherein a pulse length of the reversible current is configured according to a resistive-capacitive (RC) time constant model associated with the tongue.

30. The appliance of claim 22, wherein the first and second electrodes are adapted to substantially face opposite lateral sides of the tongue.

31. The appliance of claim 22, wherein the electrical stimulation is configured to target the patient's Palatoglossus muscle.

32. The appliance of claim 22, wherein the electrical stimulation is configured to avoid targeting a hypoglossal nerve of the patient.

33. The appliance of claim 22, wherein the device is removable.

34. The appliance of claim 22, wherein at least one of the electrodes is further configured to detect snoring in the patient.

35. The appliance of claim 22, wherein at least a portion of each of the first and second electrodes is adapted to be positioned posterior to a last molar location of the patient when the appliance is inserted within the oral cavity.

* * * * *